United States Patent [19]

Tomonaga et al.

[11] 4,222,128
[45] Sep. 16, 1980

[54] COMPOSITE IMPLANT MATERIALS AND PROCESS FOR PREPARING SAME

[75] Inventors: Atsushi Tomonaga, Tachikawa; Hideki Aoki, Funabashi, both of Japan

[73] Assignee: Kureha Kagaku Kogyo Kabushiki Kaisha, Tokyo, Japan

[21] Appl. No.: 903,579

[22] Filed: May 8, 1978

[30] Foreign Application Priority Data

May 20, 1977 [JP] Japan .................................. 52-57553

[51] Int. Cl.³ ........................... A61C 8/00; A61F 1/00
[52] U.S. Cl. .......................................... 3/1.9; 106/35; 106/39.5; 128/92 C; 427/2; 433/201; 260/998.11; 260/37 EP
[58] Field of Search ...................... 106/39.5, 35; 32/8, 32/10 A; 3/1.9, 1.91; 128/92 R, 92 C; 427/2, 385 R, 385 B; 433/201

[56] References Cited

U.S. PATENT DOCUMENTS

| | | | |
|---|---|---|---|
| 3,628,248 | 12/1971 | Kroder et al. | 3/1.9 |
| 3,713,860 | 1/1973 | Auskern | 3/1.9 |
| 4,073,999 | 2/1978 | Bryan et al. | 128/92 C |
| 4,097,935 | 7/1978 | Jarcho | 106/39.5 |
| 4,131,597 | 12/1978 | Bluethgen et al. | 32/10 A |
| 4,171,544 | 10/1979 | Hench et al. | 3/1.9 |

*Primary Examiner*—Helen M. McCarthy
*Attorney, Agent, or Firm*—Murray and Whisenhunt

[57] ABSTRACT

Disclosed is a composite implant material comprising a sintered apatite material and a thermoplastic or thermosetting resin. Said composite material is prepared by forming a sintered apatite material and filling or impregnating a thermoplastic or thermosetting resin into the pores or holes of the sintered apatite material, which have been formed during the formation of said sintered material or perforated after the formation thereof. Said composite implant material has controlled compatibility to bone as well as excellent physical strength.

8 Claims, 3 Drawing Figures

4,222,128

COMPOSITE IMPLANT MATERIALS AND PROCESS FOR PREPARING SAME

FIELD OF THE INVENTION

The invention relates to composite implant materials, particularly composite materials of apatite useful for artificial prostheses in orthopedic and dental fields, and to a process for the preparation thereof.

BACKGROUND OF THE INVENTION

Various metallic, plastics and ceramic materials have hitherto been used as an implant material for a bone or tooth in the orthopedic and dental fields. However, these conventional materials are not satisfactory since they are poor in compatibility to bone in a human or animal body.

Apatite is represented by the formula $Ca_{10}(PO_4)_6(OH,F,Cl)_2$, which may further contain 1 to 10% of carbonate ion ($CO_3^{--}$). Such an apatite substance constitutes a main component of the minerals of bones and teeth in vertebrate and has chemical properties such as being soluble in an acid, little or slightly soluble in water and highly stable in an alkali. It is known, on the other hand, that sintered apatite materials obtainable by sintering apatite at a high temperature have no toxicity and are excellent in compatibility to bone in a human or animal body. Therefore, the sintered apatite materials have increasingly become of great interest in the orthopedic and dental fields. However, the sintered apatite materials have insufficient mechanical strength, paricularly low impact strength, and therefore, must be improved in strength in order to make it possible to employ them as an implant material for a part to which body weight is to be loaded, for example (see, H. Aoki et al, Ceramics, "Apatite as a Biomaterial", 10 [7] 1975, PP. 57-66).

SUMMARY OF THE INVENTION

It has now been found that the use of a plastics material in combination with a sintered apatite material makes it possible not only to improve the strength inherent to the sintered apatite material but, also, to moderately control the compatibility of the sintered apatite material to bone, and; hence, composite materials of a sintered apatite material with a plastics material can provide very useful implant materials.

Thus, the principal object of the present invention is to provide composite implant materials which can avoid the above-mentioned drawbacks encountered with the conventional implant materials and are excellent in both physical and chemical properties.

According to the present invention, a composite implant material comprises a sintered apatite material and a thermoplastic or thermosetting resin, at least said sintered apatite material existing in a continuous phase and the respective phases of said sintered apatite material and said thermoplastic or thermosetting resin being exposed, in part, to the surface of said implant material.

The present invention also provides a process for preparing the composite implant material according to the invention, which process comprises forming a sintered apatite material and filling or impregnating a thermoplastic or thermosetting resin into the pores or holes of the sintered apatite material, which have been formed during the formation of said sintered apatite material or perforated into a desired configuration after the formation of said sintered apatite material.

DESCRIPTION OF PREFERRED EMBODIMENTS

Figure 1:
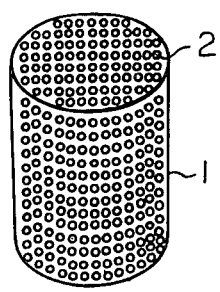
FIGS. 1 through 3 schematically illustrate the embodiments of the arrangement of the sintered apatite material phase and the thermoplastic or thermosetting resin phase in the composite implant material formed into a columnar shape.
Figure 2:
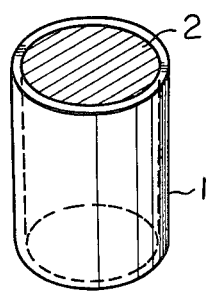
Figure 3:
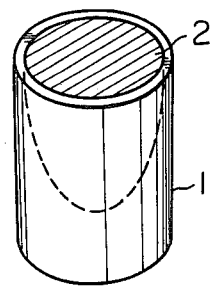

Apatite to be employed in the present invention may preferably be hydroxyapatite ($Ca_{10}(PO_4)_6(OH)_2$). Hydroxyapatite may contain a certain amount of whitlockite ($Ca_3(PO_4)_2$), if desirable from the view point of the affinity to bone or the strength. The preparation and the sintering of apatite may be carried out, for example, by a method as described in the Japanese publication hereinbefore mentioned. The sintered apatite material may, thus, be obtained in a porous or dense state. The composition of the resulting sintered apatite material can be desirably controlled by appropriately selecting the composition of the starting material or the condition for the preparation or sintering of apatite. Likewise, the porosity of the resulting sintered apatite material can also be desirably controlled.

The thermoplastic or thermosetting resins usable for the present invention may be selected from those which are well known in the art. Examples of such resins include polyethylene, polypropylene, polymethyl methacrylate, polyurethane, polyester, acrylonitrile-butadiene-styrene resins, fluorocarbons, polyamides, polyacetals, polycarbonate, polysulfone, epoxy resins, silicone resins, diallyl phthalate resins and furan resins. These resins may contain reinforcing materials such as carbon, silicon carbide, glass, alumina, magnesia, zirconia, tungsten, molybdenum, stainless steel and the like, and other fillers. It is desirable that these resins and reinforcing materials be selected so as to provide desired properties, such as mechanical strength and stability, to the resulting composite material, according to the intended use thereof. However, it is important that they be selected in careful consideration of innocuity against a living body and of good processability.

Where the sintered apatite material is as dense as to have a porosity of not more than 20%, the resin may not be or very scarcely be impregnated into the sintered apatite material. However, where the sintered apatite material has a porosity above 20%, the resin may be directly impregnated into the pores of the sintered apatite material. That is to say, in the process of the present invention, the sintered apatite material may be formed into a porous state so that the resin may be impregnated into the pores to obtain a composite material. Alternatively, if the sintered apatite material is so dense that the resin may not be impregnated, or if an additional amount of the resin is to be impregnated, or the resin is to be filled into the sintered apatite material in a desired configuration, the sintered apatite material may be formed with a desired porosity, perforated into a desired configuration by mechanical perforation, or chemical treatment, or by perforation by means of an ultrasonic wave vibration, laser, water jet or the like, and then, filled or impregnated with the resin into the pores or holes. Then, the resin may be hardened or cured by a conventional method.

In the resultant composite implant material according to the present invention, the sintered apatite material, thus, exist in a continuous phase, which is desirable since the sintered apatite material phase is exposed onto the major part of the surface of the composite implant material.

The embodiments of the arrangement of the sintered apatite material phase and the thermoplastic or thermosetting resin phase in a columnar shaped composite implant material according to the invention are schematically illustrated in the accompanying drawings. In the figures, 1 denotes the sintered apatite material phase and 2 denotes the resin phase. Naturally, the configuration of the composite implant material of the present invention is not limited to those as shown in these figures. For example, the resin may be filled or impregnated in various configurations according to the configurations of the pores or holes formed during the preparation of the sintered apatite material or perforated after the formation of the sintered apatite material.

The composite apatite materials according to the present invention are excellent in both physical and chemical properties. They can be obtained as a molded article in a prescribed shape and, hence, are very suitable as an implant material for orthopedic and dental uses. They can be safely buried in a human or animal body as a prosthesis for a bone or tooth damaged by an accident or by a disease such as bone tumor, dental carries or serious periodontic disease, and intimately bound to a vital tissue without any rejection phenomena while maintaining the high strength thereof.

Further, the composite implant materials according to the invention have a surprising advantage in that their compatibility to bone can be controlled as desired. Upon the use of an implant material for the replacement of a bone or tooth, particularly of a tooth root, it may be necessary to take out the buried implant material from the living body immediately when any troubles are found after the implantation of the material. In such a case, it is very important that the implant material has a moderate affinity for bone, in order to make it possible to take out the implanted material as required.

The following example will further illustrate the present invention.

EXAMPLE

A. 74 g of purified $Ca(OH)_2$ was stirred into 2 l of distilled water. To the obtained suspension, 2 l of a solution of about 70 g of 80% phosphoric acid in distilled water was slowly added, to adjust the pH value to approximately 7.0, and they were reacted at 25° C., for 1 hour with stirring. Then, the reaction mixture was allowed to stand at room temperature for 24 hours. The reaction product was then collected through centrifuging and dried. The obtained dry powder was microcrystalline calcium phosphate having a Ca/P ratio of about 1.6, which had a composition and construction analogous to those of stoichiometrical hydroxyapatite having a Ca/P ratio of 1.67.

Then, the calcium phosphate powder was blended with an amount of $Ca(OH)_2$ sufficient to supplement the deficiency of calcium as compared with stoichiometrical hydroxyapatite and they were reacted at 800° C. in the air. The X-ray diffraction and the thermal analysis of the resultant powder proved that it was pure crystalline hydroxyapatite, stable even at a high temperature of up to 1400° C.

B. The hydroxyapatite powder obtained as mentioned above was dressed into a grain size of 250 mesh and, then, press molded, under 1,000 $kg/cm^2$, for 5 minutes, into a column of a diameter of 10 mm. The column was then sintered in the air, at 1300° C., for 3 hours.

The sintered product thus obtained had a density corresponding to about 95% of the theoretical density (which corresponds to a porosity of about 5%), a compressive strength of about 1,500 $kg/cm^2$ and a flexural strength of 700 $kg/cm^2$.

C. The sintered apatite column was perforated by means of ultrasonic wave vibration so as to obtain the holes of the shape and arrangement as seen in FIG. 1 with an opening percentage (a percentage of the volume of the holes to the whole volume) of about 30%. The perforated column was impregnated under vacuum, at 80° C., for 30 minutes, with an epoxy resin having a composition of, 100 parts by weight of an epoxy resin (Epon 828 available from Shell Chemical Co.), 90 parts by weight of a curing agent (methyl nadic anhydride), 2 parts by weight of a curing accelerator (tri-(dimethylamino)-methylphenol), and the resin was cured at 160° C., for 3 hours.

The columnar composite material thus obtained had a compressive strength and flexural strength approximately equivalent to those as mentioned in B, above. A block sample of a composite material of a size of 10×10×5 mm, produced by the procedure as mentioned above, was dropped from a height of 10 m onto a concrete surface to prove the excellent impact strength of the composite material of the invention. The sample was not broken at all. A sample of an article of the same size consisting of only the sintered apatite material produced as mentioned above was broken into three pieces in the above-mentioned test.

D. The composite column thus obtained was buried in a tooth extraction fovea of an adult dog as an artificial tooth root. Observation for a period of one month proved that the column was non-toxic and moderately bound to the mandibula of the dog.

What we claim is:

1. A composite implant material usable as a prosthesis for a bone or tooth, comprising a perforated sintered apatite material having perforation holes formed therein in a desired configuration and a thermoplastic or thermosetting resin, at least said perforated sintered apatite material existing in a continuous phase, said resin being filled or impregnated into said holes, and the respective phases of said sintered apatite material and said resin being exposed, in part, to the surface of said implant material.

2. A composite implant material according to claim 1, wherein said sintered apatite material comprises hydroxyapatite.

3. A composite implant material according to claim 1, wherein said thermoplastic or thermosetting resin is selected from the group consisting of polyethylene, polypropylene, polymethyl methacrylate, polyurethane, polyester, acrylonitrile-butadiene-styrene resins, fluorocarbons, polyamides, polyacetals, polycarbonate, polysulfone, epoxy resins, silicone resins, diallyl phthalate resins and furan resins.

4. A composite implant material according to claim 3, wherein said resin contains a reinforcing material selected from carbon, silicon carbide, glass, alumina, magnesia, zirconia, tungsten, molybdenum and stainless steel.

5. A process for preparing a composite implant material according to claim 1, comprising forming a sintered apatite material, perforating the sintered apatite material to form holes in a desired configuration therein, and filling or impregnating a thermoplastic or thermosetting resin into said holes.

6. A process according to claim 5, wherein said sintered apatite material is formed using hydroxyapatite.

7. A process according to claim 5, wherein said thermoplastic or thermosetting resin is selected from the group consisting of polyethylene, polypropylene, polymethyl methacrylate, polyurethane, polyester, acrylonitrile-butadiene-styrene resins, fluorocarbons, polyamides, polyacetals, polycarbonate, polysulfone, epoxy resins, silicone resins, diallyl phthalate resins and furan resins.

8. A process according to claim 5, wherein said sintered apatite material is perforated by mechanical perforation or chemical treatment, or by perforation by means of ultrasonic wave, laser or water jet.

* * * * *